United States Patent
Liu et al.

(10) Patent No.: US 10,940,465 B2
(45) Date of Patent: Mar. 9, 2021

(54) ACID-RESISTANT ALLOY CATALYST

(71) Applicants: Changchun Meihe Science and Technology Development Co., LTD, Jilin (CN); The Coca-Cola Company, Atlanta, GA (US)

(72) Inventors: Jing Liu, Changchun (CN); Hongbin Qi, Changchun (CN); Haiyu Ren, Marietta, GA (US); Indra Prakash, Alpharetta, GA (US); Yu Shi, Marietta, GA (US)

(73) Assignees: The Coca-Cola Company, Atlanta, GA (US); Changchun Meihe Science and Technology Development Co., LTD

( * ) Notice: Subject to any disclaimer, the term of this patent is extended or adjusted under 35 U.S.C. 154(b) by 0 days.

(21) Appl. No.: 16/742,479

(22) Filed: Jan. 14, 2020

(65) Prior Publication Data
US 2020/0254427 A1    Aug. 13, 2020

Related U.S. Application Data

(63) Continuation of application No. 15/514,984, filed as application No. PCT/CN2015/090323 on Sep. 23, 2015, now Pat. No. 10,556,226.

(30) Foreign Application Priority Data

Sep. 28, 2014 (CN) .......................... 2014 1 0512717

(51) Int. Cl.
*B01J 23/10* (2006.01)
*B01J 25/02* (2006.01)
(Continued)

(52) U.S. Cl.
CPC .......... *B01J 25/02* (2013.01); *B01J 37/0072* (2013.01); *B01J 37/08* (2013.01); *C07C 29/132* (2013.01); *C07C 31/20* (2013.01); *C07C 31/22* (2013.01)

(58) Field of Classification Search
CPC ........ B01J 25/02; B01J 37/0072; B01J 37/08; C07C 29/132
(Continued)

(56) References Cited

U.S. PATENT DOCUMENTS 8,324,433 B2    12/2012  Zhang et al.
2005/0244312 A1  11/2005  Suppes
(Continued)

FOREIGN PATENT DOCUMENTS

CN          1683293       10/2005
CN        101199930        6/2008
(Continued)

OTHER PUBLICATIONS

Liu et al. Machine translation of CN101199930. Jun. 18, 2008 (Year: 2008).*
(Continued)

*Primary Examiner* — Haytham Soliman
(74) *Attorney, Agent, or Firm* — King & Spalding

(57) ABSTRACT

Disclosed is an acid-resistant alloy catalyst comprising nickel, one or more rare earth elements, stannum and aluminum. The acid-resistant alloy catalyst is low-cost and stable, and does not need a carrier, and can be stably used in continuous industrial production, thus achieving a low production cost.

13 Claims, 1 Drawing Sheet

(51) Int. Cl.
　　*C07C 31/22*　　(2006.01)
　　*C07C 31/20*　　(2006.01)
　　*B01J 37/00*　　(2006.01)
　　*B01J 37/08*　　(2006.01)
　　*C07C 29/132*　　(2006.01)

(58) Field of Classification Search
　　USPC .......................................................... 502/304
　　See application file for complete search history.

(56) References Cited

U.S. PATENT DOCUMENTS

| | | | |
|---|---|---|---|
| 2012/0172588 A1 | 7/2012 | Qiao Ming et al. | |
| 2012/0172633 A1* | 7/2012 | Zhang | C07C 29/132 568/861 |
| 2015/0057469 A1 | 2/2015 | Zhang et al. | |
| 2017/0210687 A1 | 7/2017 | Liu et al. | |

FOREIGN PATENT DOCUMENTS

| | | |
|---|---|---|
| CN | 101735014 | 6/2010 |
| CN | 102190562 | 9/2011 |
| CN | 102643165 | 8/2012 |
| CN | 102675045 | 9/2012 |
| CN | 102731258 | 10/2012 |
| CN | 103848720 | 6/2014 |
| JP | 3293846 | 6/2002 |
| KR | 20020024848 | 4/2002 |
| WO | WO 2008071090 | 6/2008 |
| WO | WO 2013170767 | 11/2013 |
| WO | WO 2015154258 | 10/2015 |

OTHER PUBLICATIONS

International Search Report for PCT/CN2015/090321, dated Dec. 23, 2015.
International Search Report for PCT/CN2015/090323, dated Jan. 4, 2016.
Extended European Search Report for EP15844730, dated May 2, 2018.
Extended European Search Report for EP15844083, dated Apr. 23, 2018.
Chapparo, et al. "Data results and operational experience with a solar hydrogen system," J. Power Sources, vol. 144, No. 1, 2005, pp. 165-169.
Zhijun, T., et al. "Catalytic Conversion of Cellulose to Ethylene Glycol over a Low-Cost Binary Catalyst of Raney Ni and Tungstic Acid", CHEMSUSCHEM, vol. 6, No. 4, 2013, pp. 652-658.
Avelino Corma, et al., "Chemical Routes for the Transformation of Biomass into Chemicals" Chemical Reviews, vol. 107, No. 6, 2007, pp. 2411-2502.
Mingyuan Zheng, et al., "One-pot catalytic conversion of cellulose to ethylene glycol and other chemicals: From fundamental discovery to potential commercialization", Chinese J. Catalysis 35, 2014, pp. 602-613.
Yan, L., et al. "Studies on Mechanism of Sucrose Decomposition in Impure Sugar Solutions", China and Beet Sugar, 1996, pp. 11-16. (English abstract).
Liu et al. Machine translation of CN101199930. Jun. 18, 2008.
Extended European Search Report for EP 19206794.0, dated Mar. 23, 2020.

* cited by examiner

ACID-RESISTANT ALLOY CATALYST

TECHNICAL FIELD

The present invention relates to an alloy catalyst, in particular to an acid-resistant alloy catalyst.

BACKGROUND ART

Due to their strong adsorption of hydrogen, high catalytic activity and thermal stability, Raney nickel alloy catalysts are widely used in many industrial processes and organic synthesis reactions, such as hydrogenation reactions of the unsaturated compounds olefins, alkynes, nitriles, diolefins, aromatics, carbonyl-containing substances, and even macromolecules with unsaturated bonds, as well as hydrogenation reactions of soluble sugars, such as the hydrogenation of soluble sugars to produce sorbitol and xylitol. Acid is produced in the course of some reactions; under acidic conditions, nickel releases hydrogen and thereby produces nickel ions $Ni^{2+}$, with the result that the catalyst slowly dissolves and loses its hydrogenating activity. In general, an alkali must be added to the reaction system to neutralize acid, in order to maintain the stability of the nickel catalyst. The addition of alkali will not only increase the cost of the alkali starting material, but also increase the cost of product separation and purification, and will even change the selectivity of the catalyst for the target product. For example, in a reaction in which ethylene glycol is prepared by direct hydrocracking of sugar, since sugar very readily undergoes a hydrolysis side reaction under high-temperature aqueous phase conditions, small-molecule substances such as acetic acid, lactic acid and formic acid are produced, causing an increase in the acidity of the system (Sevilla M, Fuertes A B. Chemical and structural properties of carbonaceous products obtained by hydrothermal carbonization of saccharides. Chemistry-A European Journal. 2009, 15(16): 4195-4203.); it is reported in the literature that the stability of the nickel-containing catalyst can be maintained by regulating the pH of the reaction system at 7 or above (CN 103667365 A). However, under high pH conditions, the yield of propylene glycol will significantly increase while the yield of ethylene glycol will significantly decrease (U.S. Pat. No. 5,107,018, CN 101781167 A, CN 101781171 A, CN 101781166 A); at the same time, acids produced in the hydrolysis side reaction such as formic acid, acetic acid and lactic acid increase, and the total diol yield will correspondingly fall (CN 101544537 A).

Under acidic conditions of pH<5, reducing sugars are in a more stable state, and essentially do not undergo a hydrolysis side reaction (Li Yan, Shen Canqiu et al., Research on the decomposition mechanism of sucrose in impure sugar solutions, China Beet and Sugar, 1996(2): 11-16); thus, the polyol yield of a sugar hydrogenation catalytic system can be increased if the latter operates under acidic conditions. However, under low pH conditions, only precious metals such as Ru and Pt are stable, so can be used as catalytically active components. The use of precious metals will significantly increase the diol production cost. To reduce the amount of precious metal used and increase catalytic activity, supports with a high specific surface area are generally selected to fix and disperse it. However, commonly used supports, for example inorganic oxides such as alumina, silica and magnesia, are unstable under acidic conditions, and readily undergo a neutralization reaction and dissolve in the reaction system, leading to a fall in the polyol yield (CN 103159587 A). Being an acid-resistant material, activated carbon is also commonly used as a catalyst support, to increase the specific surface area of the catalyst (CN 103420796 A, CN 102643165 A, CN 102731258 A, CN 10161325 A). However, activated carbon is also unstable under high-temperature hydrogen conditions, and readily undergoes a hydrogenation reaction in which it is methanized (US 2002/0169344).

Furthermore, nickel alloy materials also include Hastelloys, the principal composition of which is Ni 50-64%, Mo 15-30% and Cr 14-21%. It has an extraordinary capacity for resisting various industrial chemistry environments, and in particular is capable of resisting corrosion by various organic acids; the high molybdenum and chromium contents increase the corrosion resistance thereof. As a corrosion-resistant metal structural material, it lays more emphasis on ensuring mechanical properties.

Thus, there is a need to develop an acid-resistant, cheap and stable nickel alloy catalyst which has no need for a support, can be stably used in continuous industrial production, and can lower the cost of production.

CONTENT OF THE INVENTION

The object of the present invention is to provide an acid-resistant alloy catalyst. It can be stably used in continuous industrial production, and can lower the cost of production.

The present invention employs the following technical solution:

An acid-resistant alloy catalyst, comprising nickel, one or more rare earth elements, tin and aluminium; the parts by weight of the components are preferably 10-90 parts, 1-5 parts, 1-60 parts and 5-9 parts respectively.

The acid-resistant alloy catalyst of the present invention is cheap, stable, and requires no support.

In this text, rare earth elements is a collective term for 17 chemical elements, with atomic numbers 21, 39 and 57-71, in group IIIB of the periodic table, including lanthanum (La), cerium (Ce) and samarium (Sm) etc.

Furthermore, the acid-resistant alloy catalyst comprises nickel, one or more rare earth elements, tin, aluminium and tungsten; the parts by weight of the components are preferably 10-90 parts, 1-5 parts, 1-60 parts, 5-9 parts and 1-90 parts respectively.

Furthermore, the acid-resistant alloy catalyst comprises nickel, one or more rare earth elements, tin, aluminium, tungsten and molybdenum; the parts by weight of the components are preferably 10-90 parts, 1-5 parts, 1-60 parts, 5-9 parts, 1-90 parts and 0.5-20 parts respectively.

Furthermore, the acid-resistant alloy catalyst comprises nickel, one or more rare earth elements, tin, aluminium, tungsten, molybdenum, and boron or phosphorus; the parts by weight of the components are preferably 10-90 parts, 1-5 parts, 1-60 parts, 5-9 parts, 1-90 parts, 0.5-20 parts and 0.01-5 parts respectively.

With regard to the acid-resistant alloy catalyst of the present invention, an active metal powder with a high specific surface area can be prepared directly by chemical reduction or electrolytic deposition; alternatively, a metal alloy is first formed by smelting, then metal powder is formed by mechanical pulverizing or atomizing, etc., and finally, an active metal powder is formed by a conventional Raney nickel catalyst activation method. For example, in parts by weight, 10-90 parts, 1-5 parts, 1-60 parts, 5-9 parts, 1-90 parts, 0.5-20 parts and 0.01-5 parts of nickel, rare earth element, tin, aluminium, tungsten, molybdenum, and boron or phosphorus respectively are added to a smelting furnace;

the temperature is raised to 1500-2000° C., then the temperature is lowered, and after thorough mechanical stirring to achieve uniformity, the furnace is emptied, to obtain the metal alloy. A hammer grinder is used to pulverize the metal alloy into metal powder, which is then immersed for 1-2 hours in a 20 wt %-25 wt % aqueous sodium hydroxide solution at 70-95° C., to form an active metal powder with a high specific surface area.

The acid-resistant alloy catalyst of the present invention is used in a process in which a diol is prepared by one-step catalytic hydrocracking of soluble sugar.

The method uses sugar and hydrogen as starting materials, which are brought into contact with a catalyst in water to prepare a diol; the catalyst used is a composite catalyst, consisting of a main catalyst and a cocatalyst, wherein
the main catalyst is the acid-resistant alloy catalyst of the present invention;
the cocatalyst is a soluble tungstic acid salt and/or an insoluble tungsten compound.

Preferably, the diol is ethylene glycol.

The acid-resistant alloy catalyst of the present invention is used as a main catalyst, which is used in cooperation with a cocatalyst of a soluble tungstic acid salt and/or an insoluble tungsten compound, to catalyse sugar as a composite catalyst to obtain a diol; the yield of diol, in particular ethylene glycol, can be ensured at a low production cost. The acid-resistant alloy catalyst of the present invention is stable under acidic conditions, and there is no need to add an alkali to the reaction system to neutralize acid formed by hydrolysis of sugar. In continuous industrial production, the use of such an acid-resistant alloy catalyst as a main catalyst is especially important for the long-term, stable operation of the system and for control of production costs.

Preferably, when ethylene glycol is prepared by the method described above, the reaction system pH is 1-7; more preferably, the reaction system pH is 3-6. By keeping the system pH<7, not only can a hydrolysis side reaction of starting material sugar during the reaction be avoided, thereby reducing the amount of starting material sugar consumed in ethylene glycol production, but also the service life of the catalyst is ensured, so the cost of using the catalyst can be reduced, and the stability of long-term continuous operation of the reaction system can be ensured; at the same time, the ethylene glycol yield is high, and the output of organic acids and polymers is low. If acids produced in the course of the reaction are not enough to maintain a low pH, inorganic acids or organic acids such as lactic acid, formic acid and acetic acid may be added to the system to regulate the pH of the reaction system. Generally, organic acid or inorganic acid is added together with starting material sugar.

Preferably, the sugar is selected from one or more of five-carbon monosaccharides, disaccharides and oligosaccharides, six-carbon monosaccharides, disaccharides and oligosaccharides, soluble five-carbon polysaccharides, and soluble six-carbon polysaccharides. Original sources of the starting material sugar include but are not limited to sugar-based substances such as beet and sugarcane, starch-based substances such as maize, wheat, barley and cassava, lignocellulose-based substances such as maize straw, corn cobs, wheat straw, sugarcane dregs and timber, cellulosic industrial residue such as corn cob dregs, or polysaccharide substances including algae, etc. In this text, soluble five-carbon polysaccharides and soluble six-carbon polysaccharides are five-carbon polysaccharides and six-carbon polysaccharides which can dissolve under the reaction conditions of this process, not just five-carbon polysaccharides and six-carbon polysaccharides which can dissolve at room temperature.

Preferably, the sugar reacts with hydrogen in the form of an aqueous sugar solution (abbreviated as sugar solution), and the aqueous sugar solution has a concentration of 5-60 wt %, more preferably 20-50 wt %. In a continuous operation, the sugar solution may be fed continuously by means of a delivery pump. A suitable catalyst is selected so that the restriction imposed on starting material sugar concentration by the reaction system is smaller; sugar solution of high concentration may be used as a starting material, and this will significantly reduce the production cost of diol, in particular ethylene glycol, thereby realizing large-scale and economical diol production.

Preferably, the soluble tungstic acid salt is one or more of ammonium tungstate, sodium tungstate and sodium phosphotungstate; the insoluble tungsten compound is tungsten trioxide and/or tungstic acid.

The main catalyst is mixed with water and then added to a reactor.

Preferably, the amount of the main catalyst used is 0.01-10 times the amount of sugar fed per hour.

Preferably, the reaction is in continuous mode.

Preferably, the amount of the main catalyst added is: 0.01-5 kg of main catalyst added per 1000 kg of sugar fed. The addition of catalyst may be realized by discharging a portion of old catalyst through a catalyst output valve (generally at the bottom of the reactor), then adding the same amount of new catalyst through a catalyst feed valve (generally at the bottom of the reactor).

The soluble cocatalyst may be first added to sugar solution, then these may be added to the reactor together. Preferably, the amount of the soluble cocatalyst used is 0.01-5 wt % of the aqueous sugar solution, more preferably 0.01-2 wt %, and most preferably 0.01-1 wt %.

The insoluble cocatalyst may be added to the reactor together with the main catalyst. Preferably, the amount of the insoluble cocatalyst used is 0.5-50 wt % of the main catalyst, more preferably 5-20 wt %.

Preferably, the reaction system has a reaction pressure of 5-12 MPa, a reaction temperature of 150-260° C., and a reaction time 10 min.

More preferably, the reaction system has a reaction pressure of 6-10 MPa, a reaction temperature of 180-250° C., and a reaction time of 0.5-3 h. The reaction time is most preferably 0.5-2 hours.

Preferably, the reaction takes place in a slurry bed reactor. To ensure that the reaction proceeds smoothly, the total volume of reaction liquid formed does not exceed 80% of the reactor volume.

Preferably, a filter is provided in the slurry bed reactor, for causing an insoluble portion of the catalyst to be retained in the reactor, and not carried away by gas and reaction liquid flowing out through the filter.

Before the reaction begins, main catalyst is added to the slurry bed reactor, and hydrogen and sugar solution are added to the reactor at the same time using respective pumps, and a reaction takes place; the addition of sugar and main catalyst is in a continuous flow state, and reaction liquid flows out of the reactor continuously. Regarding the cocatalyst, when it is a soluble tungsten compound, it is added to the reactor together with sugar solution; when it is an insoluble tungsten compound, it is added to the reactor at the same time as the main catalyst. A filter is installed in the reactor. The filter can intercept catalyst, but gas and reaction liquid will flow out continuously through the filter and enter a condenser to undergo gas/liquid separation. Crude hydrogen undergoes purification to remove CO, $CO_2$ and $CH_4$ etc., and becomes purified hydrogen again, returning to the reactor. Effluent flowing out of the condenser enters a separation system, and is separated to obtain water, ethylene glycol, propylene glycol, butylene glycol, glycerol, sorbitol and cocatalyst, etc. Products such as ethylene glycol, propylene glycol and butylene glycol may be obtained by purification using existing technology (e.g. rectification). Water, sorbitol, glycerol and cocatalyst that is already dissolved in the reaction system are returned to the reactor to react in a cycle.

DESCRIPTION OF THE ACCOMPANYING DRAWINGS

PARTICULAR EMBODIMENTS

Figure 1:
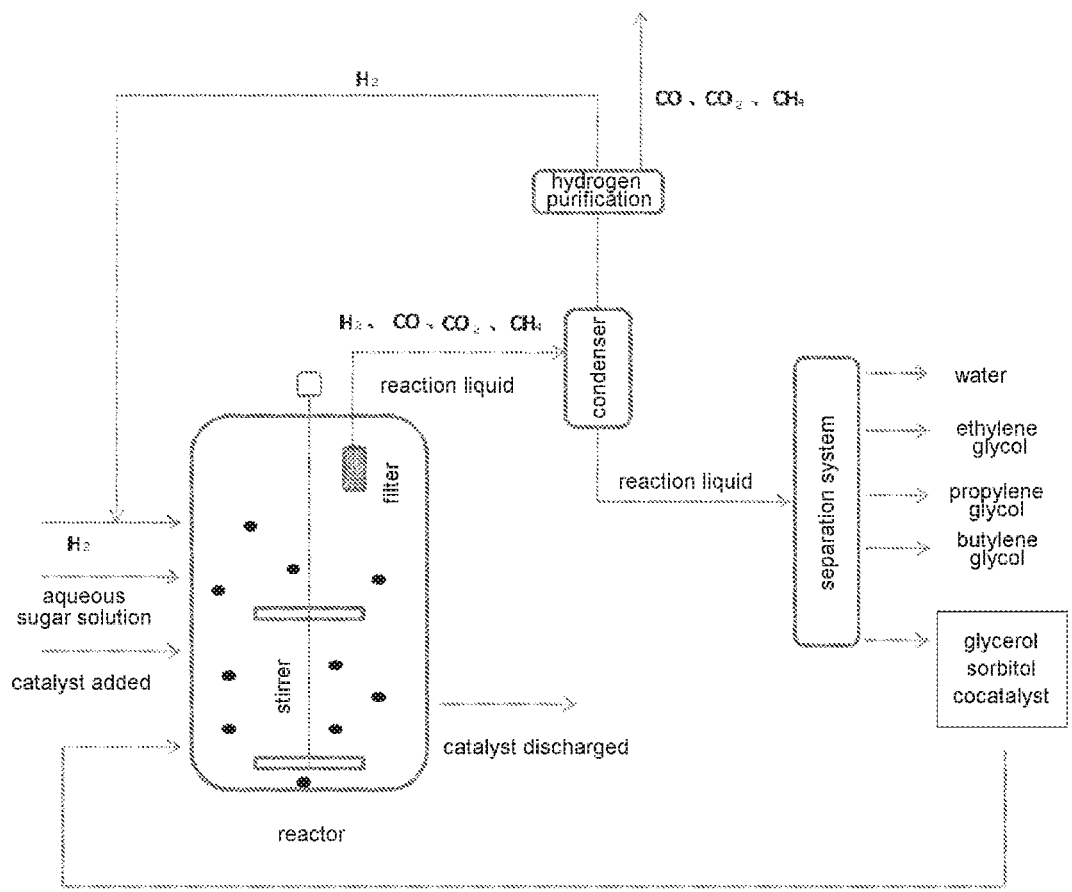
FIG. 1 is a schematic diagram of the process flow when the acid-resistant alloy catalyst of the present invention is used in the one-step catalytic hydrocracking of soluble sugar to prepare diols.

The present invention is explained further below in conjunction with the accompanying drawings and embodiments.

Embodiment 1

Preparation of Acid-Resistant Alloy Main Catalyst:

With regard to the acid-resistant alloy catalyst of the present invention, an active metal powder with a high specific surface area can be prepared directly by chemical reduction or electrolytic deposition; alternatively, a metal alloy is first formed by smelting, then metal powder is formed by mechanical pulverizing or atomizing, etc., and finally, an active metal powder is formed by a conventional Raney nickel catalyst activation method. For example, in parts by weight, 10-90 parts, 1-5 parts, 1-60 parts, 5-9 parts, 1-90 parts, 0.5-20 parts and 0.01-5 parts of nickel, rare earth element, tin, aluminium, tungsten, molybdenum, and boron or phosphorus respectively are added to a smelting furnace; the temperature is raised to 1500-2000° C., then the temperature is lowered, and after thorough mechanical stirring to achieve uniformity, the furnace is emptied, to obtain the metal alloy. A hammer grinder is used to pulverize the metal alloy into metal powder, which is then immersed for 1-2 hours in a 20 wt %-25 wt % aqueous sodium hydroxide solution at 70-95° C., to form an active metal powder with a high specific surface area.

An acid-resistant alloy catalyst Ni80La1Sn30Al5 (indicating that the composition of the acid-resistant alloy catalyst is 80 parts Ni+1 part La+30 parts Sn+5 parts Al, likewise below), an acid-resistant alloy catalyst Ni10Sm5Sn3Al9W70Mo5, an acid-resistant alloy catalyst Ni70Ce1Sn50Al7W5Mo1B5, an acid-resistant alloy catalyst Ni90Ce3Sn60Al9W20Mo5B1, an acid-resistant alloy catalyst Ni10Sm5Sn10Al9W90, an acid-resistant alloy catalyst Ni90Ce3Sn60Al9W20Mo20P0.01, and an acid-resistant alloy catalyst Ni80La1Ce0.5Sn30Al5 are prepared separately.

Embodiment 2

6 L of water and 1000 g of acid-resistant alloy catalyst Ni80La1Sn30Al5 (as a main catalyst) are added to a 10 L reaction kettle while stirring. The reaction kettle is sealed, hydrogen is passed in for 5 hours at 1000 L/h at atmospheric pressure to replace air in the reaction kettle, then the hydrogen pressure is raised to 10 MPa, and hydrogen is passed in for a further 5 hours, the reaction kettle temperature is raised to 250° C., and continuous feeding begins. The feed composition is: 50 wt % glucose, 2 wt % sodium tungstate, 48 wt % water, and the density of the sugar solution is about 1.23 $g/cm^3$; the feed rate is 3 L/h. The residence time of sugar in the reaction kettle is 2 hours. Acetic acid is added to the reaction kettle such that the reaction system pH is 3.5. Reaction liquid and hydrogen after the reaction flow out of the reaction kettle through a filter into a condensing tank; the output speed of reaction liquid is 3 L/h, and reaction liquid is discharged from the bottom of the condensing tank after cooling, to give effluent. The effluent enters a rectification separation system, and water, ethylene glycol, propylene glycol, glycerol and sorbitol and sodium tungstate are respectively obtained, wherein heavy components that are not distilled out, including glycerol and sorbitol and sodium tungstate, are returned to the reaction system to react in a cycle. A sample is taken at the bottom of the condensing tank, and the composition thereof is detected by high performance liquid chromatography.

A conventional technique may be used for the high performance liquid chromatography detection. The present invention provides the following experimental parameters for reference:

Instrument: Waters 515 HPLC Pump;

detector: Water 2414 Refractive Index Detector;

chromatography column: 300 mm×7.8 mm, Aminex HPX-87H ion exchange column;

mobile phase: 5 mmol/L sulphuric acid solution;

mobile phase flow rate: 0.6 ml/min;

column temperature: 60° C.;

detector temperature: 40° C.

Results: the glucose conversion rate is 100%; the diol yield is 77%, wherein the ethylene glycol yield is 71%, the propylene glycol yield is 7%, and the butylene glycol yield is 3%; the methanol and ethanol yield is 5%, and other yields are 14%.

FIG. 1 is a schematic diagram of the process flow when the acid-resistant alloy catalyst of the present invention is used in the one-step catalytic hydrocracking of soluble sugar to prepare diols.

Figure 2:
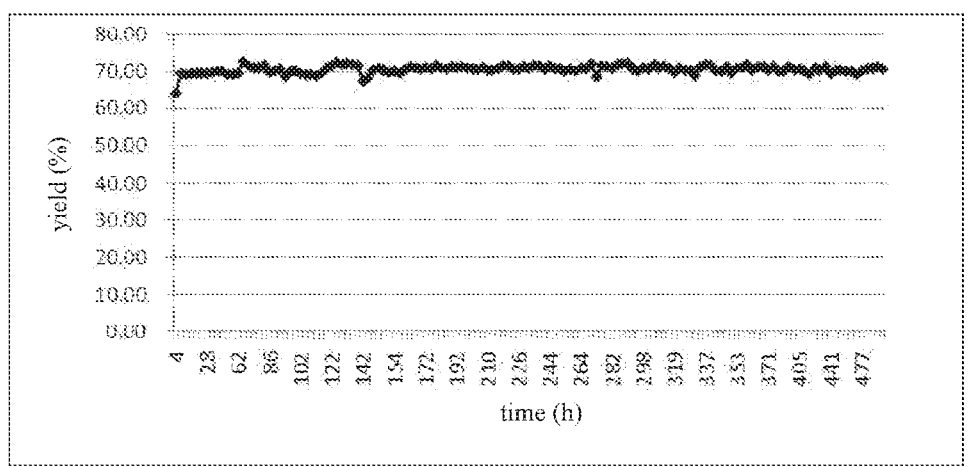
FIG. 2 is a graph of the variation of ethylene glycol yield with time in embodiment 2.

FIG. 2 is a graph of the variation of ethylene glycol yield with reaction system operation time. It can be seen from the figure that the ethylene glycol yield is substantially maintained at about 70%. This indicates that the composite catalyst can ensure that the ethylene glycol yield is still stable after 500 hours of continuous operation of the reaction system.

When the reaction system pH is changed to 9, the results are: the glucose conversion rate is 100%; the diol yield is 68%, wherein the ethylene glycol yield is 38%, the propylene glycol yield is 27%, and the butylene glycol yield is 3%; the methanol and ethanol yield is 5%, and other yields are 27%.

Embodiment 3

The acid-resistant alloy catalyst is Ni10Sm5Sn3Al9W70Mo5, and the amount added is 5000 g.

The feed composition is: 15 wt % glucose, 0.01 wt % ammonium tungstate, 84.9 wt % water, and the density of the sugar solution is about 1.06 g/cm$^3$.

Reaction system pH=6.

Other operating conditions are the same as in embodiment 2.

Results: the glucose conversion rate is 100%; the diol yield is 66%, wherein the ethylene glycol yield is 61%, the propylene glycol yield is 3%, and the butylene glycol yield is 2%; the methanol and ethanol yield is 9%, and other yields are 25%.

Embodiment 4

The acid-resistant alloy catalyst is Ni70Ce1Sn50Al7W5Mo1B5, and the amount added is 500 g.

The amount of tungsten trioxide added is 100 g.

The feed composition is: 40 wt % glucose, 60 wt % water, and the density of the sugar solution is about 1.18 g/cm$^3$.

Reaction system pH=4.2.

Other operating conditions are the same as in embodiment 2.

Results: the glucose conversion rate is 100%; the diol yield is 70%, wherein the ethylene glycol yield is 67%, the propylene glycol yield is 2%, and the butylene glycol yield is 1%; the methanol and ethanol yield is 9%, and other yields are 21%.

Embodiment 5

The acid-resistant alloy catalyst is Ni90Ce3Sn60Al9W20Mo5B1, and the amount added is 1000 g.

The feed composition is: 15 wt % xylose, 40 wt % glucose, wt % maltose, 1 wt % maltotriose, 1 wt % sodium phosphotungstate, 42 wt % water, and the density of the sugar solution is about 1.22 g/cm$^3$.

Reaction system pH=4.8.

Other operating conditions are the same as in embodiment 2.

Results: the conversion rate of xylose, glucose, maltose and maltotriose is 100%; the diol yield is 75%, wherein the ethylene glycol yield is 60%, the propylene glycol yield is 11%, and the butylene glycol yield is 4%; the methanol and ethanol yield is 7%, and other yields are 18%. After 500 hours of catalyst operation, the ethylene glycol yield is still stable.

Embodiment 6

The acid-resistant alloy catalyst is Ni90Ce3Sn60Al9W20Mo5B1, and the amount added is 5000 g.

The feed composition is: 50 wt % xylose, 0.1 wt % sodium tungstate, 49.9 wt % water, and the density of the sugar solution is about 1.21 g/cm$^3$.

Reaction system pH=4.8.

Other operating conditions are the same as in embodiment 2.

Results: the conversion rate of xylose is 100%; the diol yield is 67%, wherein the ethylene glycol yield is 49%, the propylene glycol yield is 16%, and the butylene glycol yield is 2%; the methanol and ethanol yield is 12%, and other yields are 21%. After 500 hours of catalyst operation, the ethylene glycol yield is still stable.

Embodiment 7

The acid-resistant alloy catalyst is Ni10Sm5Sn10Al9W90, and the amount added is 180 g.

The feed composition is: 60 wt % glucose, 2 wt % sodium tungstate, 38 wt % water, and the density of the sugar solution is about 1.29 g/cm$^3$.

The reaction pressure is 12 MPa, and the reaction temperature is 260° C.

Other operating conditions are the same as in embodiment 2.

Results: the conversion rate of glucose is 100%; the diol yield is 75%, wherein the ethylene glycol yield is 65%, the propylene glycol yield is 7%, and the butylene glycol yield is 3%; the methanol and ethanol yield is 11%, and other yields are 14%.

Embodiment 8

The acid-resistant alloy catalyst is Ni90Ce3Sn60Al9W20Mo20P0.01, and the amount added is 5 g.

The feed composition is: 5 wt % glucose, 0.05 wt % sodium tungstate, 94.95 wt % water, and the density of the sugar solution is about 1.02 g/cm$^3$.

Reaction system pH=1.

The reaction pressure is 6 MPa, and the reaction temperature is 180° C.

Other operating conditions are the same as in embodiment 2.

Results: the conversion rate of glucose is 100%; the diol yield is 65%, wherein the ethylene glycol yield is 53%, the propylene glycol yield is 9%, and the butylene glycol yield is 3%; the methanol and ethanol yield is 4%, and other yields are 31%.

Embodiment 9

The acid-resistant alloy catalyst is Ni80La1Ce0.5Sn30Al5; other operating conditions are the same as in embodiment 2.

Results are similar to those of embodiment 2.

Embodiment 10

The acid-resistant alloy main catalyst is Ni70Sm1Sn10Al7W5Mo0.5, and the amount added is 1500 g.

The feed composition is: 40 wt % glucose, 60 wt % water, 0.5 wt % sodium tungstate, and the density of the sugar solution is about 1.18 g/cm$^3$.

Reaction system pH=4.2.

Other operating conditions are the same as in embodiment 2.

Results: the conversion rate of glucose is 100%; the diol yield is 87%, wherein the ethylene glycol yield is 80%, the propylene glycol yield is 5%, and the butylene glycol yield is 2%; the methanol and ethanol yield is 3%, and other yields are 10%.

Clearly, the abovementioned embodiments of the present invention are merely examples given to explain the present invention clearly, and by no means define the embodiments of the present invention. A person skilled in the art could make other changes or modifications in different forms on the basis of the explanation above. It is not possible to list all embodiments here exhaustively. All obvious changes or modifications extended from the technical solution of the present invention shall still fall within the scope of protection of the present invention.

The invention claimed is:

1. A composite catalyst comprising (i) an acid-resistant alloy catalyst consisting essentially of, in parts by weight, 10-90 parts nickel, 1-5 parts rare earth element, 1-60 parts tin and 5-9 parts aluminium and (ii) a cocatalyst consisting of a soluble tungstic acid salt and/or an insoluble tungsten compound.

2. A composite catalyst comprising (i) an acid-resistant alloy catalyst consisting essentially of, in parts by weight, 10-90 parts nickel, 1-5 parts rare earth element, 1-60 parts tin, 5-9 parts aluminium and 1-90 parts tungsten and (ii) a cocatalyst consisting of a soluble tungstic acid salt and/or an insoluble tungsten compound.

3. A composite catalyst comprising (i) an acid-resistant alloy catalyst consisting essentially of, in parts by weight, 10-90 parts nickel, 1-5 parts rare earth element, 1-60 parts tin, 5-9 parts aluminium, 1-90 parts tungsten and 0.5-20 parts molybdenum and (ii) a cocatalyst consisting of a soluble tungstic acid salt and/or an insoluble tungsten compound.

4. A composite catalyst comprising (i) an acid-resistant alloy catalyst consisting essentially of, in parts by weight, 10-90 parts nickel, 1-5 parts rare earth element, 1-60 parts tin, 5-9 parts aluminium, 1-90 parts tungsten, 0.5-20 parts molybdenum, and 0.01-5 parts boron or phosphorus and (ii) a cocatalyst consisting of a soluble tungstic acid salt and/or an insoluble tungsten compound.

5. The composite catalyst of claim 1, wherein the rare earth elements are a collective term for 17 chemical elements, with atomic numbers 21, 39 and 57-71, in group IIIB of the periodic table.

6. The composite catalyst of claim 1, wherein the cocatalyst is a soluble tungstic acid salt selected from the group consisting of ammonium tungstate, sodium tungstate, sodium phosphotungstate and a combination thereof.

7. The composite catalyst of claim 1, wherein the cocatalyst is an insoluble tungsten compound selected from the group consisting of tungsten trioxide, tungstic acid and a combination thereof.

8. The composite catalyst of claim 2, wherein the cocatalyst is a soluble tungstic acid salt selected from the group consisting of ammonium tungstate, sodium tungstate, sodium phosphotungstate and a combination thereof.

9. The composite catalyst of claim 2, wherein the cocatalyst is an insoluble tungsten compound selected from the group consisting of tungsten trioxide, tungstic acid and a combination thereof.

10. The composite catalyst of claim 3, wherein the cocatalyst is a soluble tungstic acid salt selected from the group consisting of ammonium tungstate, sodium tungstate, sodium phosphotungstate and a combination thereof.

11. The composite catalyst of claim 3, wherein the cocatalyst is an insoluble tungsten compound selected from the group consisting of tungsten trioxide, tungstic acid and a combination thereof.

12. The composite catalyst of claim 4, wherein the cocatalyst is a soluble tungstic acid salt selected from the group consisting of ammonium tungstate, sodium tungstate, sodium phosphotungstate and a combination thereof.

13. The composite catalyst of claim 4, wherein the cocatalyst is an insoluble tungsten compound selected from the group consisting of tungsten trioxide, tungstic acid and a combination thereof.

* * * * *